(12) United States Patent
Tomcany

(10) Patent No.: US 7,360,264 B2
(45) Date of Patent: Apr. 22, 2008

(54) PATIENT IMMOBILIZATION DEVICE WITH DIAGNOSTIC CAPABILITIES

(76) Inventor: Brian Tomcany, 19431 Blue Spruce Dr., Strongsville, OH (US) 44149

( * ) Notice: Subject to any disclaimer, the term of this patent is extended or adjusted under 35 U.S.C. 154(b) by 170 days.

(21) Appl. No.: 11/103,256

(22) Filed: Apr. 11, 2005

(65) Prior Publication Data

US 2006/0225213 A1 Oct. 12, 2006

(51) Int. Cl.
*A61F 5/37* (2006.01)
*A61G 1/04* (2006.01)

(52) U.S. Cl. .................... 5/622; 5/637; 5/628

(58) Field of Classification Search ............ 5/622, 5/621, 637, 636, 625–629; 128/845, 846, 128/869, 870
See application file for complete search history.

(56) References Cited

U.S. PATENT DOCUMENTS

| | | | |
|---|---|---|---|
| 2,377,940 A | 6/1945 | Hughes | |
| 2,391,928 A | 1/1946 | Seib | 5/82 |
| 2,394,264 A | 2/1946 | Robinson | 5/82 |
| 2,511,061 A | 6/1950 | Hughes | |
| 2,675,564 A | 4/1954 | Hughes | |
| 2,770,465 A | 11/1956 | Dandurand | 280/12 |
| 3,222,080 A | 12/1965 | Kinraide | 280/18 |
| 3,449,776 A | 6/1969 | Brock | 5/627 |
| 3,467,085 A * | 9/1969 | Cormier | 606/203 |
| 3,650,523 A | 3/1972 | Darby, Jr. | 5/603 |
| 3,653,079 A | 4/1972 | Bourgraf et al. | 5/82 |
| 3,689,945 A | 9/1972 | Laerdal | 5/82 |
| 3,707,734 A | 1/1973 | Matthews | 5/82 |
| 3,737,923 A | 6/1973 | Prolo | 5/82 |
| 3,775,782 A | 12/1973 | Rice et al. | 5/82 |
| 3,890,659 A | 6/1975 | Staubs | 5/82 |
| 4,024,861 A | 5/1977 | Vincent | 128/87 |
| 4,033,000 A | 7/1977 | Bonifay | 5/82 |
| 4,033,339 A * | 7/1977 | Roberts et al. | 602/18 |
| 4,064,574 A | 12/1977 | Schnitzler | 5/82 |
| 4,118,868 A * | 10/1978 | Johnson | 33/512 |
| 4,124,908 A | 11/1978 | Burns et al. | 5/82 |
| 4,166,459 A * | 9/1979 | Nightingale | 602/35 |
| 4,252,113 A | 2/1981 | Scire | 5/628 |
| 4,267,830 A | 5/1981 | Vick | 128/87 |
| 4,347,635 A | 9/1982 | Eisenhauer | 441/40 |

(Continued)

FOREIGN PATENT DOCUMENTS

GB 2215059 A * 9/1989

OTHER PUBLICATIONS

Alliance Medical Catalog, *Morrison Medical New & Improved Head Vise™ II Head Immobilizer*, http://www.allmed.net/catalog/showitem.php/3445, Sep. 29, 2002, p. 1.

(Continued)

*Primary Examiner*—Robert G. Santos
(74) *Attorney, Agent, or Firm*—Wood, Herron & Evans LLP

(57) ABSTRACT

A patient immobilization device for immobilizing a patient and performing a diagnostic evaluation of such patient is comprised of a backboard, a structure configured to support the head of a patient on the backboard, and a pupil-sizing indicator positioned on a surface of the support structure to be visually accessible to a person that is visually evaluating the head and face of an immobilized patient on the backboard.

9 Claims, 4 Drawing Sheets

U.S. PATENT DOCUMENTS

| | | | | |
|---|---|---|---|---|
| 4,369,982 | A | | 1/1983 | Hein et al. ............... 280/47.13 |
| 4,463,758 | A | * | 8/1984 | Patil et al. .................. 606/130 |
| 4,480,345 | A | | 11/1984 | Dunn ............................... 5/82 |
| 4,517,747 | A | * | 5/1985 | Morin .......................... 33/512 |
| 4,571,757 | A | | 2/1986 | Zolecki .......................... 5/628 |
| 4,592,352 | A | * | 6/1986 | Patil ............................ 606/130 |
| 4,696,220 | A | | 9/1987 | Pagliaro ........................ 84/453 |
| 4,736,736 | A | * | 4/1988 | Moers et al. .................. 602/18 |
| 4,771,493 | A | | 9/1988 | Park |
| 4,794,656 | A | | 1/1989 | Henley, Jr. ....................... 5/82 |
| 4,854,305 | A | * | 8/1989 | Bremer ......................... 602/32 |
| 4,928,711 | A | | 5/1990 | Williams .................... 128/869 |
| 5,133,217 | A | * | 7/1992 | Jordan .................... 73/862.452 |
| 5,201,089 | A | | 4/1993 | Ferreira .......................... 5/627 |
| 5,211,185 | A | | 5/1993 | Garth et al. ................ 128/870 |
| 5,233,713 | A | * | 8/1993 | Murphy et al. ................. 5/636 |
| 5,265,625 | A | | 11/1993 | Bodman ..................... 128/869 |
| 5,395,158 | A | | 3/1995 | Cordia ........................ 297/393 |
| 5,410,769 | A | * | 5/1995 | Waterman ....................... 5/632 |
| 5,414,883 | A | | 5/1995 | Fangrow, Jr. ................... 5/625 |
| D367,834 | S | | 3/1996 | Beavers et al. ............ D12/133 |
| 5,534,952 | A | * | 7/1996 | Zanecchia et al. .......... 351/200 |
| 5,657,766 | A | | 8/1997 | Durham ...................... 128/870 |
| 5,729,850 | A | | 3/1998 | Eskeli ............................ 5/621 |
| D403,423 | S | | 12/1998 | Bologovsky et al. ...... D24/190 |
| 5,944,016 | A | | 8/1999 | Ferko, III ................... 128/869 |
| 5,947,981 | A | * | 9/1999 | Cosman ...................... 606/130 |
| 5,950,627 | A | | 9/1999 | Bologovsky et al. ....... 128/869 |
| D425,992 | S | | 5/2000 | Davis et al. ................ D24/189 |
| 6,143,003 | A | * | 11/2000 | Cosman ...................... 606/130 |
| 6,159,169 | A | * | 12/2000 | Lambden ..................... 601/15 |
| 6,170,486 | B1 | | 1/2001 | Islava .......................... 128/869 |
| 6,244,270 | B1 | | 6/2001 | Lutian et al. ............... 128/869 |
| 6,327,723 | B1 | | 12/2001 | Knight ........................... 5/628 |
| D462,448 | S | | 9/2002 | Huttner ..................... D24/191 |
| 6,443,157 | B1 | | 9/2002 | Sargent ...................... 128/870 |
| D469,541 | S | | 1/2003 | Cheatham ................. D24/191 |
| 6,565,577 | B2 | * | 5/2003 | Cosman ...................... 606/130 |
| 6,637,057 | B2 | | 10/2003 | Phillips et al. |
| 6,659,104 | B2 | | 12/2003 | Kiefer et al. ............... 128/870 |
| 6,862,759 | B2 | | 3/2005 | Hand et al. ..................... 5/430 |
| 6,964,103 | B2 | * | 11/2005 | Chudek et al. ............. 33/27.02 |
| 7,036,167 | B2 | * | 5/2006 | Tomcany et al. .............. 5/628 |
| 2003/0159216 | A1 | * | 8/2003 | Tomcany et al. .............. 5/628 |
| 2004/0016057 | A1 | | 1/2004 | Traut et al. |
| 2004/0049852 | A1 | | 3/2004 | Phillips et al. |
| 2005/0050744 | A1 | * | 3/2005 | Chudek et al. ............. 33/27.02 |
| 2005/0229313 | A1 | * | 10/2005 | Tomcany et al. .............. 5/628 |
| 2005/0241068 | A1 | * | 11/2005 | Tomcany et al. .............. 5/622 |
| 2006/0225213 | A1 | * | 10/2006 | Tomcany .......................... 5/622 |

OTHER PUBLICATIONS

Alliance Medical Catalog, *Laerdl® BaXstrap® Spineboard*, http://www.allmed.net/catalog/showitem.php/3454, Sep. 29, 2002, p. 1.
Alliance Medical Catalog, *Allied LSP HDx® Backbaoard*, http://www.allmed.net/catalog/showitem.php/3453, Sep. 29, 2002, pp. 1-2.
Alliance Medical Catalog, *Dispos-A-Board® Backboard*, http://www.allmed.net/catalog/showitem.php/3463, Sep. 29, 2002, pp. 1-2.
Alliance Medical Catalog , *Bashaw Rough Terrain CID*, http://www.allmed.net/catalog/showitem.php/3434, Sep. 29, 2002, p. 1.
Alliance Medical Catalog, *Allied LSP SpinX® Backboard*, http://www.allmed.net/catalog/showitem.php/3449, Sep. 29, 2002, p. 1.
Alliance Medical Catalog, *Allied LSP Stabilizer® Backboard*, http://www.allmed.net/catalog/showitem.php/3450, Sep. 29, 2002, p. 1.
Alliance Medical Catalog, *I-Tec® Multi-Grip Head Immobilizer*, http://www.allmed.net/catalog/showitem.php/3438, Sep. 29, 2002, p. 1.
Alliance Medical Catalog, *EP&R Bak-Pak*, http://www.allmed.net/catalog/showitem.php/4115, Sep. 29, 2002, p. 1.
Alliance Medical Catalog, *Morrison Medical Sticky Blocks™ Head Immobilizers*, http://www.allmed.net/catalog/showitem.php/4396, Sep. 29, 2002, p. 1.
Alliance Medical Catalog, *Morrison Medical Head Vise™ I Reusable Head Immobilizer*, http://wwww.allmed.net/catalog/showitem.php/3444, Sep. 29, 2002, p. 1.
Alliance Medical Catalog, *Bashaw Infant CID*, http://www.allmed.net/catalog/showitem.php/4124, Sep. 29, 2002, pp. 1-2.
Alliance Medical Catalog, *Morrison Medical Head Blocks?™ Set, With Straps*, http://www.allmed.net/catalog/showitem.php/4401, Sep. 29, 2002, pp. 1-2.
Alliance Medical Catalog, *Morrison Medical Head Vise™ III*, http://www.allmed.net/catalog/showitem.php/4410, Sep. 29, 2002, p. 1.
Alliance Medical Catalog, *Morrison Medical Head Blocks™, Disposable Foam*, http://www.allmed.net/catalog/showitem.php/4398, Sep. 29, 2002, p. 1.
Alliance Medical Catalog, *Laerdal® HeadBed® II Head Immobilization Device*, http://www.allmed.net/catalog/showitem.php/3432, Sep. 29, 2002, p. 1.
Alliance Medical Catalog, *Laerdal® Speedblocks® Head Immobilizer*, http://www.allmed.net/catalog/showitem.php/3431, Sep. 29, 2002, p. 1.
Alliance Medical Catalog, *STI Sta-BLok™ Head Immobilizer*, http://www.allmed.net/catalog/shoeitem.php/3446, Sep. 29, 2002, p. 1.
Pro-Lite Spineboard, *Pro-Lite Spineboard®*, http://www.allmed.net/catalog/showitem.php/3448, Sep. 29, 2002, p. 1.
Dispos-O-Bag, *Dispos-O-Bag® Head-On® Block*, http://www.allmed.net/catalog/showitem/php/3441, Sep. 29, 2002, p. 1.
Pro-Lite XT, *Pro-Lite XT®*, http://www.allmed.net/catalog/showitem.php/3447, Sep. 29, 2002, pp. 1-2.
Bound Tree, *Hoover Headblock*, http://www.boundtree.com/quickdet., Sep. 29, 2002, p. 1.
Brittany Board, *Brittany Board*, http:www.brittanyboard.com/home.html, Sep. 29, 2002, p. 1.
Ferno, *Model 455 HeadHugger™ Disposable Head Immobilizer*, http://emergency.ferno.com/immobilize/model455.htm, Sep. 29, 2002, p. 1.
Ferno , *Model 445 Universal Head Immobilizrt*, http://emergency.ferno.com/immobilize/445.htm, Sep. 29, 2002, p. 1.
Ferno, *740/750 Series Phenolic Wooden Backboards*, http://emergency.ferno.com/immobilie/model_740 _750.htm, September 29, 2002, p. 1.
Iron Duck Catalog, *Ultra Loc Backboard & Head Loc II*, http://www.ironduck.com/catalog.epl?ProductID=118, Sep. 29, 2002, pp. 1-4.
Junkin Safety Appliance Company , *Junkin Safety Backboards*, http://www.junkinsafety.com/products/backbrd.html, Sep. 29, 2002, pp. 1-2.
Ferno, *Millenia™ Plastic Backboards*, http://emergency.ferno.com/immobilize/bckbrds.htm, Sep. 29, 2002, p. 1.
Morrison Medical, *Morrison Medical—Head Immobilzers*, http://www.mossisonmed.com/head.htm, Sep. 29, 2002, pp. 1-2.
NAJO™ Backboards , *NAJO™ Backboards*, http://reefmedical.com./au/najo, Sep. 29, 2002, pp. 1-3.
PMX, *PMX Backboard*, http://www.pmxmedical.com/catalog/page30.html, Sep. 29, 2002, p. 1.
Reefmedical, Ambu® NAJO™ Head Wedge, http:// reefmedical.com.au/headwedge.htm, Sep. 29, 2002, pp. 1-2.
Reeves, *The Reeves Sleeve®*, http://www.reevesdecon.com/sleeve.htm, Sep. 29, 2002, p. 1.
Reeves, *Reeves® Spine Board*, http://www.pmxmedical.com/catalog/page30.html, Sep. 29, 2002, p. 1.

* cited by examiner

| GLASGOW SCORE |||
|---|---|---|
| EYE OPENING (E) | VERBAL RESPONSE (V) | MOTOR RESPONSE (V) |
| 4 = SPONTANEOUS<br>3 = TO VOICE<br>2 = TO PAIN<br>1 = NONE | 5 = NORMAL CONVERSATION<br>4 = DISORIENTED CONVERSATION<br>3 = WORDS, BUT NOT COHERENT<br>2 = NO WORDS ..... ONLY SOUNDS<br>1 = NONE | 6 = NORMAL<br>5 = LOCALIZES TO PAIN<br>4 = WITHDRAWS TO PAIN<br>3 = DECORTICATE POSTURE<br>2 = DECEREBRATE<br>1 = NONE |
|  |  | TOTAL = E + V + M |

PATIENT IMMOBILIZATION DEVICE WITH DIAGNOSTIC CAPABILITIES

FIELD OF THE INVENTION

This invention relates generally to a patient immobilization device including a backboard and head immobilizer used to support and immobilize injured patients.

BACKGROUND OF THE INVENTION

In various accidents involving injury to a person or patient, the patient is often immobilized at the scene for treatment and transport. This is particularly true for any apparent injury to the head, neck and/or spine of the patient. In such cases, and certainly for head/neck injuries, the head and cervical spine areas of the patient are routinely immobilized to prevent further injury during transport to a medical facility.

For such immobilization, devices such as rigid backboards are typically used to support and assist in immobilizing the patient during this time. The patient is strapped or otherwise secured to the backboard. A head immobilization device or immobilizer is also used in addition to a backboard. For example, the patient is placed on a board and stiff pillows or blocks are placed tightly on either side of his head. A combination of headstraps, chinstraps, and tapes are then tightly secured over the pillows/blocks and the board to fixedly hold the patient's head in place on the board.

Currently, there are several typical types of head immobilizers in use that are incorporated generally with a flat backboard. One type of head immobilization system utilizes a pair of reusable blocks, which are formed of a pliant, yet supportive material such as rigid foam or a suitable vinyl material. Generally, such blocks are secured to a board with hook and loop fastening structures, such as Velcro®.

Another type of immobilizer is disposable and utilizes inexpensive cardboard, which is manipulated to form a support structure for the head and neck. Generally, such a cardboard material is temporarily coupled to a backboard with an adhesive material. Other types of head immobilization systems utilize a combination of reusable and disposable elements that may be temporarily coupled to a backboard.

Although such systems have proven suitable for use with a backboard to immobilize a patient, they present other problems. While reusable foam or vinyl blocks may be relatively inexpensive, due to reuse, they must be repeatedly cleaned and maintained after each use to prevent the transmission of unsafe pathogens, either through blood or other bodily fluid, such as vomit. Repeated cleaning of the blocks may cause premature deterioration of the blocks and their covering or outer skin. As such, after a certain amount of use, even reusable blocks will need to be replaced.

Another problem with such reusable blocks is that they are difficult to store when not in use. Separation of key pieces of the patient immobilization equipment for the purpose of storage can often lead to lost or misplaced items. This is particularly critical at an accident or medical emergency when the retrieval time may be critical for the patient's health and well being.

During patient treatment at an accident scene, or on the way to a hospital, emergency medical personnel will often have to perform evaluations regarding the medical condition of the patient. In doing so, they may need to refer to medical references and other data. This often distracts them from patient attention, however briefly, or delays them in their triage efforts. Coupled with gathering all of the various parts or pieces for a suitable immobilization, the emergency medical worker has significant distractions that take them away from a patient.

Therefore, there is a need for a patient immobilization device that addresses various of these drawbacks. Particularly, there is a need for an immobilization device that is readily used to immobilize a patient with minimal intermediate steps. There is also a need for an immobilization device that is useful for diagnostic medical evaluation of the immobilized patient.

SUMMARY OF THE INVENTION

The present invention is directed to a patient immobilization device, which may be used for diagnostic evaluation of a patient who is immobilized on the device. The immobilization device includes a structure that may be manipulated to form a support structure for the head and neck. In one embodiment, a backboard includes one or more paddles that are mounted on the backboard and are configured to move between the storage position and the support position. In the support position, the paddles support the head and/or neck of a patient secured to a backboard. A pupil-sizing indicator is positioned on a surface of the paddle and is accessible to a person who is visibly evaluating the head and face of an immobilized patient on the backboard. In that way, the medical personnel, or other caregiver, may readily evaluate the pupils of a trauma victim right at the face of the victim for a more accurate diagnostic evaluation. In one embodiment, the pupil-sizing indicator is positioned on the surface of the paddle and is generally in the line of sight a person staring into the face of a patient whose head is supported by the paddle. The pupil-sizing indicator includes a chart with a plurality of pupil sizes and numeric indicia adjacent thereto for providing a visual comparison to the pupil of a patient on the backboard.

In another embodiment of the invention, a diagnostic tool is mounted on the backboard. The diagnostic tool is positioned to be visually accessible to a person who is visually evaluating an immobilized patient. The diagnostic tool may include a diagnostic scale associated with at least one patient response from the group including eye opening, verbal response, and motor response. For example, a Glasgow Coma scale might be utilized.

In yet another embodiment of the invention, the diagnostic tool may include a diagnostic scale related to burns on the body of a patient. For example, a Rule of Nines burn scale might be included with the diagnostic tool.

Utilizing the present invention, medical personnel may rapidly and accurately provide a diagnostic evaluation of various conditions of a trauma patient. They can do so without leaving the patient or, in various cases, even looking away from the face of the patient. Therefore, the inventive patient immobilization device provides improved diagnostic evaluation once the patient is stabilized.

BRIEF DESCRIPTION OF DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS OF THE INVENTION

Figure 1:
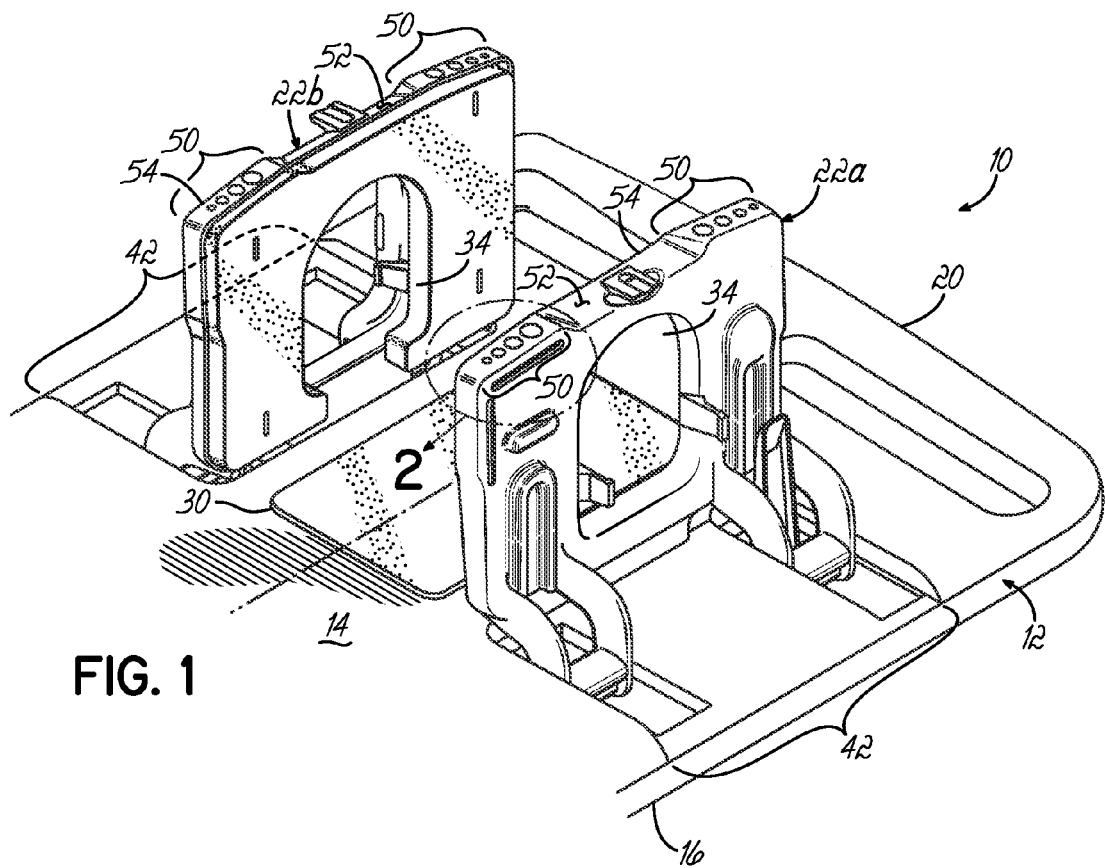
FIG. 1 illustrates a patient immobilization device in accordance with one embodiment utilizing a pupil-sizing indicator.

Referring to FIG. 1, a perspective view of an embodiment of a patient immobilization device 10 of the invention is illustrated. Generally, such a device comprises a backboard or backboard portion 12, having a top side or front side 14, and a bottom side or back side 16. The view of FIG. 1 shows a broken away section (namely the head section) of a backboard 12. It will be understood by a person of ordinary skill in the art that the backboard 12 is generally elongated to hold a patient's body, although the entire length is not shown in the Figures. In use, a patient would generally be placed on the front side 14, with their feet at a foot end (not shown) of the backboard and their head at the head end 20 of the backboard. For securing the head and neck of a patient, the invention utilizes a structure configured to support the head and neck. In one aspect, the structure may be manipulated from a storage position to a support position for use. In one embodiment, the support structure takes the form of a pair of opposing paddles 22a and 22b, which are slidably mounted on the backboard 12, and are configured, in a support position, to support the head and neck of a patient. Embodiments of the paddles 22a, 22b are illustrated in the support position in FIG. 1.

The head and neck of a patient are secured and immobilized between the paddles during use. The body of the patient lies along the length of the backboard 12, and often is secured to the backboard with straps, tape or other securement structures (not shown). The paddles are movable between a support position or upright position, as illustrated in FIG. 1, and a storage position or flat position (against the backboard 12) for storing the device 10 when not in use.

Various suitable backboards for utilizing the present invention are disclosed in U.S. patent application Ser. No. 10/335,523 entitled "Patient Immobilization Device" and filed on Dec. 31, 2002, and in U.S. patent application Ser. No. 11/101749 entitled "Patient Immobilization Device" and filed on Apr. 8, 2005. Both of these applications are incorporated herein by reference in their entireties.

The backboard 12 can be made out of wood, plastic, or any other suitable, and preferably light weight, material for supporting a patient with their head and neck immobilized between the paddles 22a, 22b.

The paddles may be made of a suitable rigid and lightweight material, such as wood or plastic. For example, a polypropylene plastic, or high-density polyethylene (HDPE) might be suitable. Paddles 22a, 22b include a layer or portion 28 of a conformable material for providing cushioning and comfort to the head of the patient while providing a level of conformability to the paddles, for better securement and immobilization of the head and neck. For example, the layer 28 might be made of a conventional foam, such as a polyurethane foam. To provide further comfort for an immobilized patient, a cushion 30 or a cushioned area between the paddles 22a, 22b might be used for cushioning the back of the head of the patient or raising the level of the head. The layer 28 or layer material may be removable, such as for cleaning purposes.

The paddles 22a, 22b and associated conformable layers 28 have openings 34 formed therein so that the patient may hear better, such as for hearing instructions from a care giver or emergency medical personnel. Often overlooked during patient transport is the patient's ability to hear. The ear holes 34 are free from obstructions, thus decreasing the possibility of miscommunication with an injured patient.

Furthermore, for diagnostic purposes in accordance with the invention, the openings 34 allow visual inspection of the ears, or fluid coming from the ears, which is often indicative of head trauma. The ear holes, or openings 34, are placed to allow for greater visualization of a patient's ear. In that way, they provide important diagnostic information about the type and extent of the injury by the type and amount of any fluid drainage of the ear.

In accordance with one aspect of the present invention, the paddles 22a, 22b are secured to the backboard 12, and remain with the device 10 not only when in use, but also when it is stored. To that end, the paddles are movable from a support position, as illustrated in FIG. 1 to a storage position, where they will lie generally flat against the backboard. In one embodiment of the invention, the paddles are essentially rotatably mounted with respect to the backboard, and rotate on an axis between the storage positions. Portions of the paddles extend through the board and along the back side and secure the paddles with the backboard. Referring to FIG. 1, in one aspect of the invention, the backboard, proximate the head end 20, forms a recess 42 to receive the paddles 22a, 22b in the storage position so that the paddles are generally flush with or below the front side surface 14 of the backboard proximate the head end 20. The paddles 22a, 22b and the recessed area 42 may be appropriately configured and dimensioned to provide an interference fit for the paddles to keep them in the storage position until needed for use.

In accordance with another aspect of the present invention, the opposing paddles 22a, 22b are also slidably mounted with respect to the backboard to adjust their positions on the backboard. When the paddles are pulled up from the storage position and toward the support position, they may then be freely slid toward each other or apart to adjust to the width of the patient's head, neck, or any other medical gear or items attached thereto. Generally, in the storage position, the paddles are at 0 degrees with respect to the front side 14 of the backboard, or with respect to the overall plane of the backboard. In the support position, as illustrated in FIG. 1, the paddles are approximately generally perpendicular to the front side 14 or to the plane of the backboard 12. Generally, they are freely slidable when moved between the storage and support positions.

Referring again to FIG. 1, the patient immobilization device 10 includes integral diagnostic capabilities, such as diagnostic tools. For example, in one embodiment, a diagnostic tool in the form of a pupil-sizing indicator 50 is positioned on a surface of the support structure, such as on the surface 52 of a paddle 22a, 22b. The pupil-sizing indicator 50 is visually accessible to a person, such as medical personnel or other emergency caregivers, who are evaluating the head and face of an immobilized patient on the backboard. As may be appreciated, a head position between paddles 22a and 22b of device 10, facing away from the backboard, will position the patient's face generally proximate the pupil-sizing indicator 50. As discussed further, the diagnostic tools might also be positioned on a surface of the backboard.

When the paddles are in the support position as illustrated in FIG. 1, they are generally perpendicular to the backboard 12. In the embodiment illustrated in FIGS. 1 and 2, the pupil-sizing indicator 50 is positioned along a top edge 54 of a paddle generally proximate to the eyes of a patient on the backboard. According to one aspect of the present invention, the pupil-sizing indicator 50 is positioned on surface 52 that is generally in the line of sight of a person staring into the face of a patient whose head is supported by the paddle. In that way, emergency personnel do not need to look away, but can direct their eyes back and forth between the eyes of the patient and the pupil-sizing indicator to make a diagnostic evaluation of pupil size, and thus determine the amount of head trauma the patient may have suffered.

The pupil-sizing indicator 50 includes a plurality of pupil sizes 56 and numeric indicia 58 adjacent thereto for providing a visual comparison to a patient on the backboard and a numeric pupil size. The pupil-sizing indicator 50 might be applied to the surface of the paddle, such as with an adhesive sticker. Alternatively, the pupil-sizing indicator might be molded directly onto the paddle 22a, 22b, and specifically onto a surface 52 of the paddle.

In the illustrated embodiment, pupil-sizing indicators 50 are provided on several spaced-apart locations on the paddles 22a, 22b. Furthermore, the pupil-sizing indicator 50 may be provided on each of the paddles 22a, 22b. In that way, regardless of the positioning of the head on the paddle, there is always a closely positioned pupil-sizing indicator 50 to make the diagnostic evaluation. With an indicator 50 on each paddle, emergency personnel may evaluate the indicator, generally in the line of sight when viewing either eye of a patient.

In accordance with another aspect of the present invention, when the pupil-sizing indicator 50 is positioned on a surface 52 of the paddle, the indicator is always readily available with the device 10. That is, emergency personnel would not need to look around or refer to other references away from the patient, to determine pupil size. Furthermore, the invention eliminates the need for emergency personnel to hold a reference proximate to the face of a patient, thereby freeing their hands for other important tasks. Upon folding the paddles up to the support position, the pupil-sizing indicator is immediately available to the line of sight of a person staring into the face of a patient. Therefore, the invention provides quick diagnostic evaluation of a trauma patient, or an injured patient, wherein the speed of diagnosis is critical.

Figures 1A, 2A:
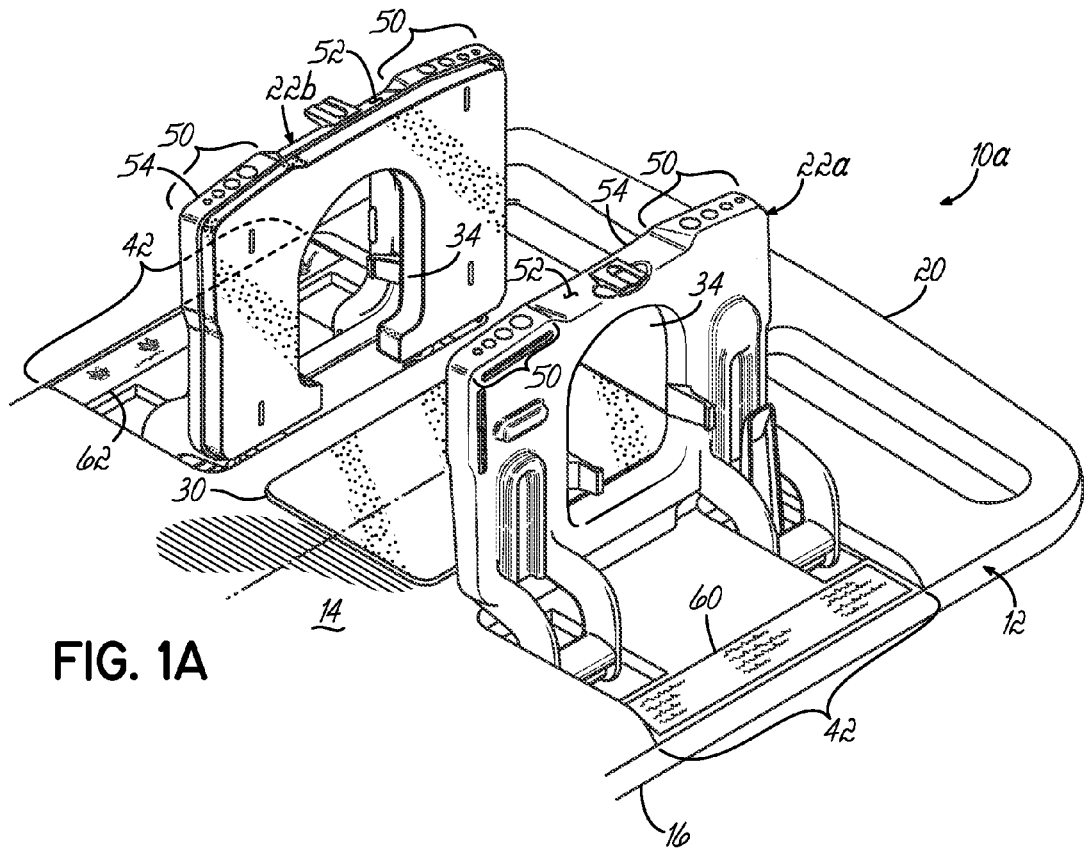
FIG. 1A illustrates a cut away portion of another embodiment of the invention utilizing a diagnostic tool mounted on the device.
FIG. 2A illustrates one embodiment of a diagnostic tool to be utilized with the patient immobilization device of FIG. 1A.

FIGS. 1A and 2A disclose an alternative embodiment of the invention. Specifically, the patient immobilization device 10a utilizes backboard 12 and paddles 22a, 22b for immobilizing a patient and supporting the head of a patient on a backboard as discussed above. Like reference numerals are utilized for the common elements between the various embodiments shown in the Figures.

The patient immobilization device 10a includes another diagnostic tool that is mounted on the backboard. The diagnostic tool 60 is shown in FIG. 1A positioned to one side of the paddle 22a to be exposed when the paddle is moved from the storage position to the support position, as shown in FIG. 1A. Actually, another diagnostic tool 62 may be utilized adjacent to paddle 22b, and is discussed further hereinbelow. Of course, only a single diagnostic tool 60 might be utilized on backboard 12. If multiple diagnostic tools 50, 60, 62 are utilized, they could be the same or similar diagnostic tools. Alternatively, as shown in FIG. 1A, different diagnostic tools 50, 60, 62 may be used to assist the medical personnel in performing several diagnostic evaluations of a patient on the backboard.

In one embodiment, as shown in FIG. 2A, the diagnostic tool 60 may include a diagnostic scale associated with at least one patient responds from a group of responses. That response group, for example, might include eye opening, verbal response, and/or motor response. The various patient responses, according to the scale, assist in the diagnostic evaluation of the patient. More specifically, a scale such as a Glasgow Coma scale 60 might be utilized as illustrated in FIG. 2A. The Glasgow Coma scale 60 has a scoring system utilized in quantifying levels of consciousness in a patient following traumatic brain injury. It is simple and straightforward and has a relatively high degree of interobserver reliability. Furthermore, the scale of the diagnostic tool 60 illustrated in FIG. 2A correlates well with the outcome following a severe brain injury.

In accordance with one aspect of the present invention, the diagnostic tool 60, 62 is mounted on the backboard and, specifically, is mounted proximate to the head of the patient. The various responses, such as eye opening, or verbal/motor responses, are directly determined at the head location of the patient. Other motor responses might be determined at various appendages or extremities. However, the diagnostic tool, being mounted on the backboard and generally mounted proximate to where it is visually accessible to a person who is visually evaluating an immobilized patient on the backboard provides a significant advantage. It eliminates medical personnel from being distracted away from the patient. Furthermore, it eliminates the step of having to refer to other separate references during diagnostic evaluation of the patient. As may be appreciated, in trauma situations and in various other emergency medical situations, rapid evaluation is necessary, as is constant and rapid attention to the patient.

The Glasgow Coma scale of diagnostic tool 60 is easy to use. Medical personnel determine the best eye opening response, the best verbal response, and the best motor response. The score then represents the sum of the numeric scores of each of the categories. Based upon the score, the medical personnel can then diagnostically evaluate the patient.

When the diagnostic tools 60 of the invention is a scale such as the Glasgow Coma scale, other factors may have to be taken into account and there may be some limitation to its use. For example, if a patient has an endotracheal tube in place, they will not be able to talk. For that reason, medical personnel may prefer to document various scores by the individual components. For example, a patient with a Glasgow Coma scale score of 15 could be documented as follows: E4 V5 M6. An Intubated patient could be scored as: E4 intubated M6. Of the various individual factors, the best motor response is generally the most significant.

Some other factors may also be taken into account with respect to the scale's ability to accurately reflect the severity of a traumatic brain injury. For example, shock, hypoxemia, drug use, alcohol intoxication and metabolic disturbances may all alter the scale independently of a brain injury. Furthermore, a patient with a spinal cord injury may make the motor skill portion invalid or a severe orbital trauma may make eye opening impossible to assess. However, the diagnostic tool 60, such as the Glasgow Coma scale, is quite useful and is a widely used scoring system used today to assess patients with a traumatic brain injury. Therefore, it is a desirable diagnostic tool to have proximate the patient and specifically proximate the head of a patient on the backboard 12.

Of course, the Glasgow Coma scale is not the only diagnostic tool that might be utilized. Various other diagnostic tools may be utilized and positioned, as shown in FIG. 1A.

Figure 2:
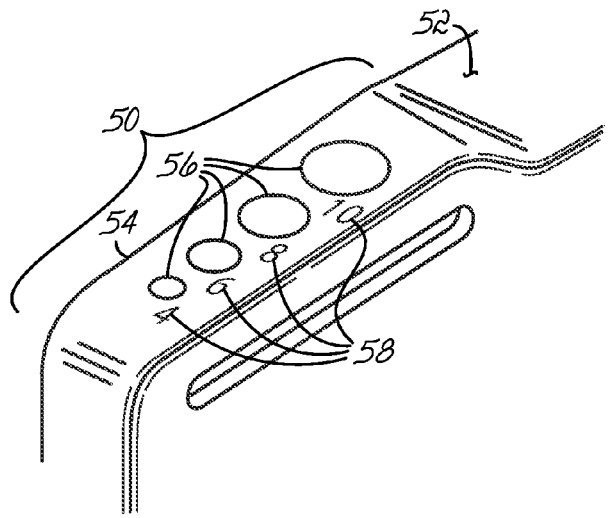
FIG. 2 is a partially cut away perspective view of a portion of the patient immobilization device of FIG. 1 illustrating one suitable pupil-sizing indicator.
Figure 1B:
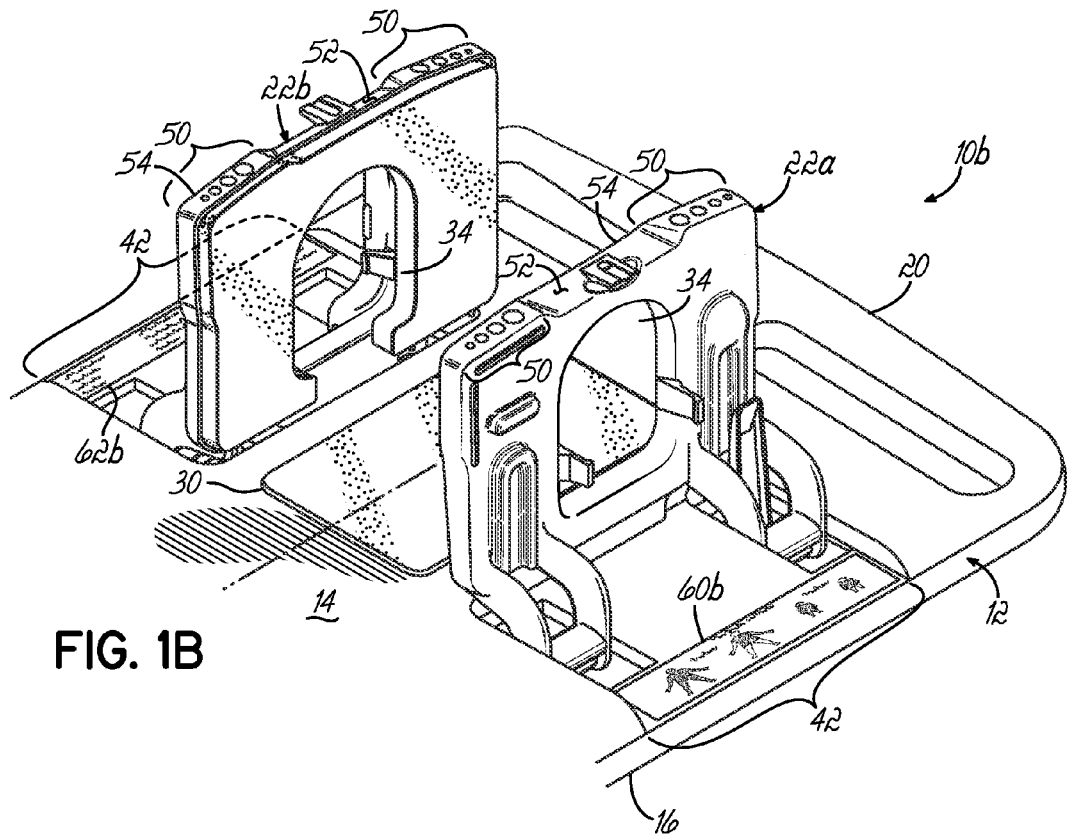
FIG. 1B illustrates a cut away portion of another embodiment of the invention utilizing a diagnostic tool mounted on the device.
Figure 2B:
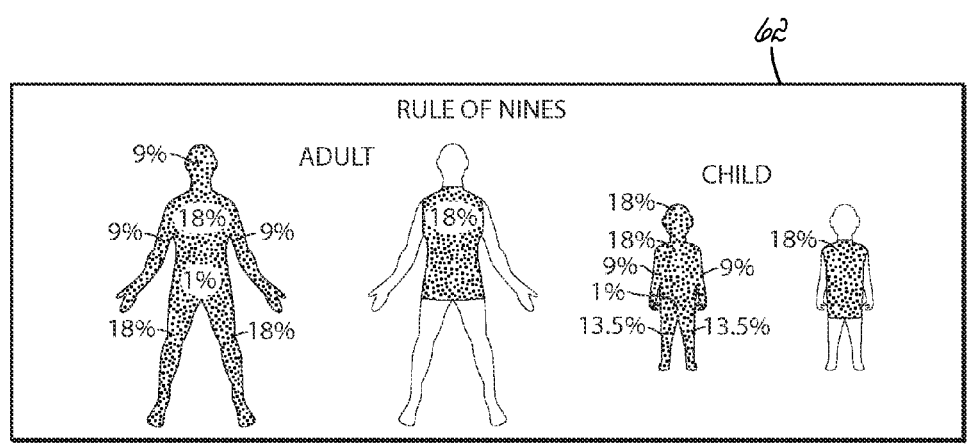
FIG. 2B illustrates one embodiment of a diagnostic tool to be utilized with the patient immobilization device of FIG. 1B.

In fact, FIGS. 1B and 2B illustrate an alternative diagnostic tool 60b that might be utilized. The diagnostic tool 60b might be related to burns on the body of a patient to provide for a diagnostic evaluation associated with such burns. For example, a Rule of Nines burn scale might be utilized as illustrated in FIG. 2B as a suitable diagnostic tool 60b.

The Rule of Nines is a method for rapidly estimating the percent of total body surface area that is affected by a burn. In burn victims, the percent of total body surface area affected is a strong predictor of a patient's overall prognosis. The Rule of Nines Scale or metric 60b helps emergency medical personnel decide whether a patient needs to be transferred to a regional burn center for specialized care. The metric 60b is also used in estimating the amount of fluid replacement the patient will need to replace losses through the burned area. Generally, the Rule of Nines derives its name from the fact that an adult body may be conveniently divided into anatomic regions that have surface area percentages that are all multiples of approximately 9 percent.

As noted, various different diagnostic tools might be utilized in the invention. For example, a backboard might include a Rule of Nines Scale 60b on one side, and a Glasgow Coma Scale 62b on the other side, as illustrated in FIG. 1B, as well as a pupil-sizing indicator 50 on a surface of structure 22a, 22b.

The diagnostic tools 60, 62, 60b, 62b may be adhered to the backboard, such as using an adhesive sticker. Generally, such an adhesive sticker would be a more permanent mounting of the diagnostic tool. Alternatively, the diagnostic tool might be removably mounted to the backboard, such as utilizing a plaque with Velcro® or another attachment method. In still another embodiment, the tool might be formed on a surface such as by being molded on the board or structures 22a, 22b. In that way, a backboard may be specifically tailored for use with different diagnostic tools mounted thereon. As noted, multiple diagnostic tools might be positioned on the same backboard. In some embodiments, the diagnostic tools are positioned proximate to or on the paddles 22a, 22b, although that is not critical, and the diagnostic tools might be mounted on the backboard other than in those positions shown in the figures. Furthermore, as the pupil-sizing indicator positioned on the surface of the paddle is illustrated in FIGS. 1 and 2, the diagnostic tools might also be mounted on the surface of the paddle.

Figure 3:
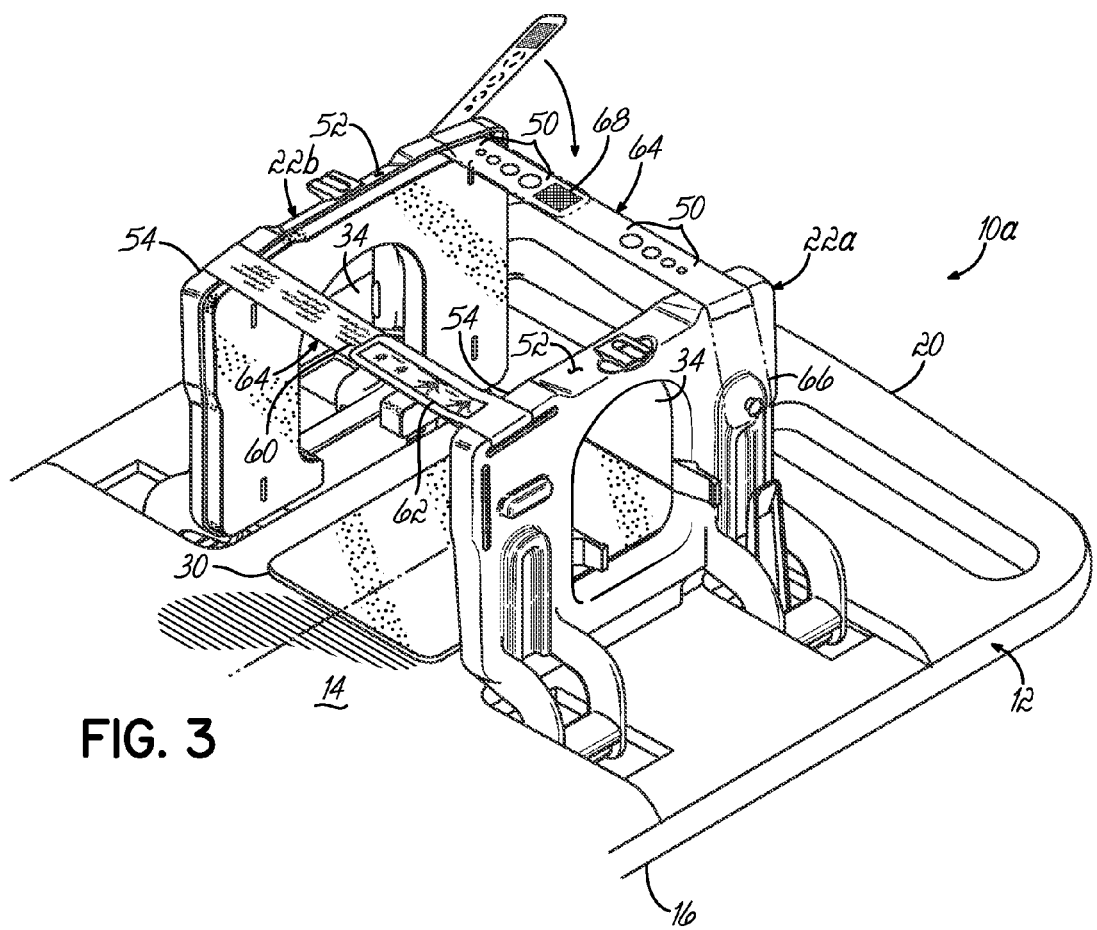
FIG. 3 illustrates another embodiment of the present invention.

In another embodiment of the invention, as illustrated in FIG. 3, one or more of the diagnostic tools might be positioned on a component of the support structure for supporting the head and neck. Specifically, the support structure, such as paddles 22a, 22b, include straps 64 that span across the head of a patient (not shown) to hold the paddles together to secure the head/neck of the patient. The paddles may be fixed or secured to a paddle at one end 66 and span across to pass through a slot or other opening in the opposite paddle. In FIG. 3, the strap 64 includes suitable fasteners such as Velcro 68 and the strap folds over on itself.

The straps may include one or more diagnostic tools thereon. In the embodiment of FIG. 3, the straps 64 include a pupil-sizing indicator 50 on one strap and other tools, such as a Glasgow scale 60 or a Rule of Nines scale 62 that are exposed when the straps are in use.

While the disclosed embodiments show backboards with integral paddles that remain with the backboard in the storage position and the support position, the present invention is also usable with any backboard, such as those flat backboards wherein separate head/neck immobilizing devices must be strapped to or otherwise affixed to the generally flat backboard. Therefore, the present invention is not limited to backboards having integral paddles as shown.

While the present invention has been illustrated by a description of various embodiments and while these embodiments have been described in considerable detail, it is not the intention of the applicant to restrict or in any way limit the scope of the appended claims to such detail. For example, various features are shown for the different embodiments, but those features do not have to all be used on a single device. Different combinations of features and components might be used on various different embodiments of the immobilization device. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed:

1. A patient immobilization device for immobilizing a patient and performing a diagnostic evaluation of such patient comprising:
   a backboard;
   a structure configured to support the head of a patient on the backboard;
   a pupil-sizing indicator positioned on a surface of the support structure to be visually accessible to a person that is visually evaluating the head and face of an immobilized patient on the backboard, the pupil-sizing indicator including a series of circular indications of varying sizes resembling the pupil of an eye for direct visual comparison to a patient pupil.

2. The device of claim 1 wherein the structure includes at least one paddle mounted on the backboard.

3. The device of claim 2 wherein the support structure includes at least one paddle mounted on the backboard and configured to move between a storage position and a support position, to support the head of a patient on the backboard.

4. The device of claim 2 wherein the support structure, in the support position, is positioned generally perpendicular to the backboard, the pupil-sizing indicator being positioned along a top edge of the support structure.

5. The device of claim 1 wherein the pupil-sizing indicator is positioned on a surface of the structure that is generally in the line of sight of a person staring into the face of a patient whose head is supported by the structure.

6. The device of claim 1 wherein the pupil-sizing indicator includes a chart with the series of circular indications of varying sizes and numeric indicia for providing a visual comparison to the pupil of a patient on the backboard.

7. The device of claim 2 wherein the pupil-sizing indicator is molded into the paddle.

8. The device of claim 2 wherein the support structure includes a pair of paddles configured for capturing the head of a patient therebetween in the support position, the paddles each having a surface extending along the side of the head, a pupil-sizing indicator positioned on each of the paddle surfaces on either side of the head.

9. The device of claim 1 further comprising multiple pupil-sizing indicators positioned on surfaces of the structure.

* * * * *